United States Patent [19]

Bradshaw et al.

[11] Patent Number: 4,975,379
[45] Date of Patent: * Dec. 4, 1990

[54] ANALYSIS OF IONS PRESENT AT LOW CONCENTRATIONS IN SOLUTIONS CONTAINING OTHER IONS

[75] Inventors: Jerald S. Bradshaw; Reed M. Izatt; Ronald L. Bruening; Virginia B. Christensen, all of Provo, Utah; Robert Alldredge, Westminster, Colo.

[73] Assignee: Brigham Young University, Provo, Utah

[ * ] Notice: The portion of the term of this patent subsequent to Jul. 24, 2007 has been disclaimed.

[21] Appl. No.: 335,591

[22] Filed: Apr. 10, 1989

[51] Int. Cl.$^5$ .......................... G01N 30/00; C02F 1/62
[52] U.S. Cl. ....................................... 436/77; 210/670; 210/662; 210/679; 210/688; 436/80; 436/81; 436/178
[58] Field of Search ............... 210/670, 672, 679, 684, 210/662, 688; 436/73, 77, 80, 81, 161, 178

[56] References Cited

U.S. PATENT DOCUMENTS 4,070,284  1/1978  Fujita et al. ..................... 436/161
4,659,512  4/1987  Macedo et al. ..................... 210/688

*Primary Examiner*—Ivars Cintins
*Attorney, Agent, or Firm*—Thorpe, North & Western

[57] ABSTRACT

The invention is a process of selectively and quantitatively removing and concentrating at least one selected ion present in low concentration with other ions in higher concentration in a multiple ion solution. The method comprises bringing a complexing agent for the selected ion(s) into contact with a different determined quantity of said multiple ion solution to remove and concentrate the selected ion(s) from the multiple ion solution; removing the multiple ion solution, from which the complexing agent has been removed, the selected ions from the complexing agent having the selected ion(s) complexed therewith, bringing the complexing agent complexed with selected ion(s) into contact with a determined quantity of receiving liquid to break the complex and remove the selected and concentrated ion(s) from the complexing agent therein, and determining the concentration of selected ion(s) in said receiving liquid from which the concentration of selected ion(s) in the multiple ion solution can be calculated. The metal ions in low concentration are often heavy metal ions, such as lead ions, and the process finds particularly advantageous utility in the determination of lead content in ppb in drinking water.

The preferred apparatus for carrying out the process is a column packed with silica gel or silica-bonded macrocycle as the complexing agent which is preferably carried out using as the complexing agent a macrocyclic compound having at least four —A—CH$_2$—CH$_2$— groups in which A is selected from —O—, —O—CH$_2$—, —S—, —S—CH$_2$—, —N—R—, and —N—((R)—CH$_2$ in which R is selected from H, lower alkyl and benzyl and which has a hydrocarbon side chain having an end group.

20 Claims, 2 Drawing Sheets

FIG. 1

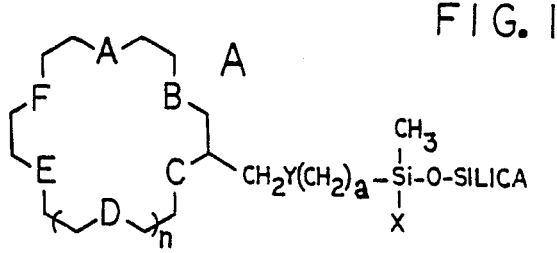

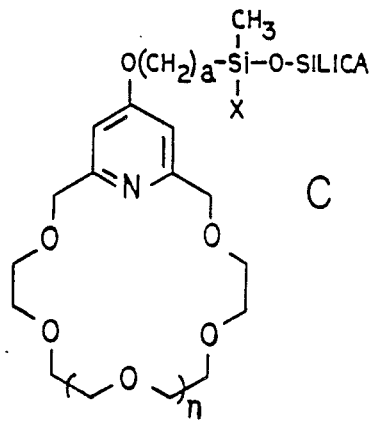

1. A-F = ANY COMBINATION OF O OR OCH$_2$ OR S OR SCH$_2$ OR N-R OR N(R)CH$_2$ (R = H OR ANY ALKYL OR BENZYL); n = -1 TO 4; X = ANY ALKYL OR Cl OR O-SILICA; Y = O OR CH$_2$; a = 1 - 16 (GENERIC)
2. A-F = O; n = 0 TO 2; X = CH$_3$ OR Cl OR O-SILICA; Y = O OR CH$_2$; a = 1 - 16 (SPECIES 1)
3. A, C, D, F = O; B AND E = N-R (R = H OR ALKYL OR BENZYL); n = 0 TO 2; X = CH$_3$ OR Cl OR O-SILICA; Y = O OR CH$_2$; a = 1 - 16 (SPECIES 2)

n = 0 TO 2;
X = CH$_3$ OR Cl OR O-SILICA;
a = 1 - 18

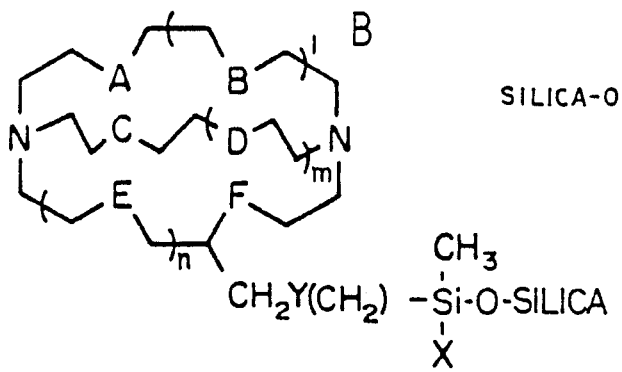

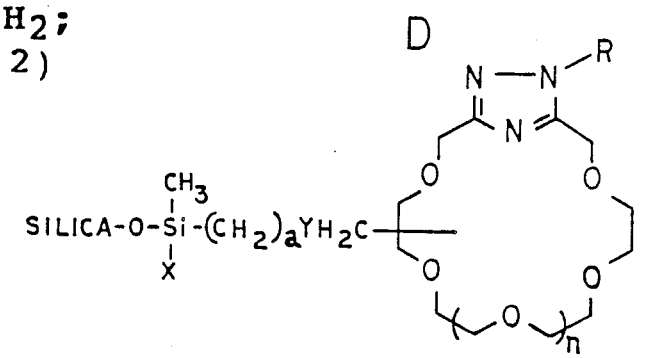

1. A-F = ANY COMBINATION OF O OR S OR N-R (R = H OR ANY ALKYL OR BENZYL); l, m, n = 0 TO 2; X = ANY ALKYL OR Cl OR O-SILICA; Y = O OR CH$_2$; a = 1 - 16 (GENERIC)
2. A-F = O; l, m, n = 1; X = CH$_3$ OR Cl OR O-SILICA; Y = O OR CH$_2$; a = 1 - 16 (SPECIES)

R = H, ANY ALKYL OR ARYL; n = 0 2; X = CH$_3$ OR Cl OR O-SILICA; Y = O OR CH$_2$; a = 1 - 16

IN WHICH SILICA IS SAND OR SILICA GEL

ANALYSIS OF IONS PRESENT AT LOW CONCENTRATIONS IN SOLUTIONS CONTAINING OTHER IONS

INTRODUCTION

The present invention relates to a method of selectively and quantitatively removing and concentrating at least one selected ion present in low concentration with other ions in a multiple ion solution which comprises bringing a complexing agent for the selected ion(s) into contact with a sufficient determined quantity of said multiple ion solution to remove the selected ion(s) from the multiple ion solution and concentrate it, removing the multiple ion solution from which the complexing agent has removed the selected ion(s) from the complexing agent having the selected ion(s) complexed therewith, bringing the complexing agent complexed with selected ion(s) into contact with a determined quantity of receiving liquid to break the complex and remove the selected and concentrated ion(s) from the complexing agent therein, and determining the concentration of selected ion(s) in said receiving liquid from which the concentration of selected ion(s) in the multiple ion solution can be calculated.

The method is particularly advantageous where the selected ion is a heavy metal ion, e.g., lead, silver, cadmium and mercury, which occurs in drinking water, often in such low concentrations as to be incapable of analysis by presently known methods but in sufficient amounts to poison people drinking the water ever a period of years.

The method is preferably carried out using as the complexing agent a macrocyclic compound having at least four —A—CH$_2$—CH$_2$— groups in which A is selected from —O—, —O—CH$_2$—, —S—, —S—CH$_2$—, —N—R—, and —N—(R)—CH$_2$— in which R is selected from H, lower alkyl and benzyl and which has a hydrocarbon side chain having an end group

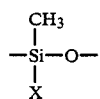

covalently bonded to silica in which X is selected from lower alkyl, benzyl, phenyl, halogen, —O—CH$_3$, —O—C$_2$H$_5$ and Si_=. Typical compounds within this generic definition consist of the following groups of compounds wherein the macrocycle is bonded to the silica through a hydrocarbon side chain with or without an ether oxygen:

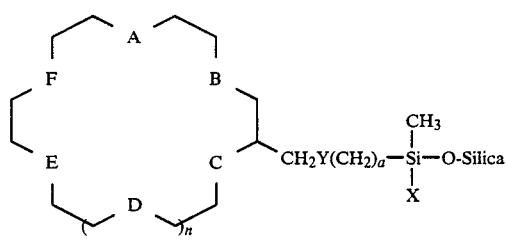

1. A–F = any combination of O or OCH$_2$ or S or SCH$_2$ or N—R or N(R)CH$_2$ (R = H or any alkyl or benzyl);
n = −1 to 4; X = any alkyl or Cl or O-Silica; Y = O or CH$_2$; a = 1-16. (Generic)

2. A–F = O; n = 0-2; X = CH$_3$ or Cl or O-Silica; Y = O or CH$_2$; a = 1-16. (Species 1)

3. A,C,D,F = O; B and E = N—R (R = H or alkyl or benzyl); n = 0-2; X = CH$_3$ or Cl or O-Silica; Y = O or CH$_2$; a = 1-16. (Species 2)

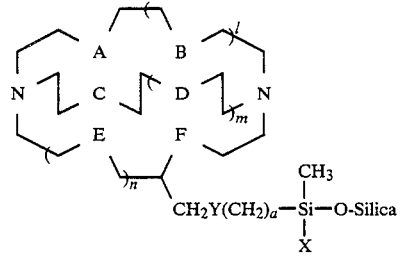

1. A–F = any combination of O or S or N—R (R = H or any alkyl or benzyl); l, m, n = 0-2; X = any alkyl or Cl or O-Silica; Y = O or CH$_2$; a = 1-16. (Generic)
2. A–F = O; l = m = n = 1; X = CH$_3$ or Cl or O-Silica; Y = O or CH$_2$; a = 1-16. (Species)

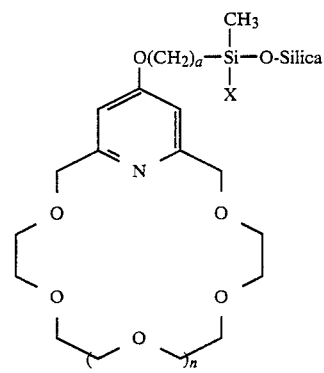

n = 0-2; X = CH$_3$ or Cl or O-Silica; a = 1-18.

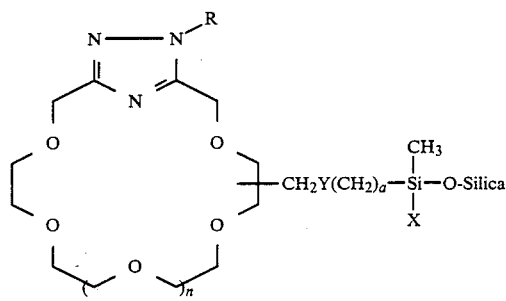

n = 0-2; R = H, any alkyl or aryl; X = CH$_3$ or Cl or O-Silica; Y = O or CH$_2$; a = 1-16.

In which Silica is sand or silica gel.

The process is particularly useful for determining the heavy metal ion content of drinking water when it is present in ppb. It comprises flowing the drinking water in measured quantity through a column packed with silica covalently bonded to a complexing agent for the heavy metal ions, flowing a determined and smaller quantity of receiving liquid through said column to break the complex and take the liberated ions into solution, analyzing the solution to determine the percent heavy metal ions therein, and calculating therefrom the concentration of heavy metal ions in the drinking water.

A preferred embodiment disclosed herein involves carrying out the process by bringing a known volume of the multiple ion solution into contact with either a macrocycle-bonded silica such as one of those shown in FIG. 1 or silica gel, depending on the ion(s) and solution conditions, in a separation column through which the mixture is first flowed, followed by the flow through the column of a much smaller known volume of a receiving liquid to break the complex, dissolve the desired ions and carry them out of the column. The concentrations of the desired ions can then be determined by well known analytical methods.

More particularly, the embodiment of the process comprises placing either silica gel or a macrocycle-bonded silica(FIG. 1) in a tall column, causing a known volume of the mixture of ions to flow through the column where the desired ions complex with the bonded or plain silica which separates them from the rest of the mixture which flows out of the column, then flowing a much smaller known volume of the receiving liquid through the column to break the complex and dissolve and carry out of the column the desired ion(s). The desired ion(s) are now present in a much more concentrated form and the concentrations of the desired ion(s) present in the receiving liquid are determined by well known analytical methods.

BACKGROUND OF THE INVENTION

The analysis of ion(s) present in water at concentrations below the 100 ppb level is generally inaccurate and/or difficult. This analysis problem is compounded when other ions are present in the same solution at much greater concentrations. Previously, we have submitted patent applications J. S. Bradshaw, R. M. Izatt and J. J. Christensen, PROTON IONIZABLE MACROCYCLIC COMPOUNDS AND SELECTIVE COMPETITIVE SEPARATION OF DESIRABLE METAL IONS FROM MIXTURES THEREOF WITH OTHER IONS, U.S. patent application Ser. No. 07/036,664 filed Apr. 8, 1987 as continuation-in-part of U.S. patent application, Ser. No. 06/859,308 filed May 5, 1986; and J. S. Bradshaw, R. M. Izatt, J. J. Christensen, and R. L. Bruening, MACROCYCLIC LIGANDS BONDED TO SILICA AND THEIR USE IN SELECTIVELY AND QUANTITATIVELY REMOVING AND CONCENTRATING IONS PRESENT AT LOW CONCENTRATIONS FROM MIXTURES THEREOF WITH OTHER IONS, U.S. patent application, Ser. No. 07/240,689, filed 09/06/88, which disclosed the bonding of macrocycles, which do not contain electron withdrawing groups, to silica via a side chain which is not connected to one of the electron rich macrocycle donor atoms (the compounds of FIG. 1). These bonded macrocycles have been shown to selectively form strong bonds with particular ions or groups of ions similar to the behavior of the same macrocycles present as solutes in solution. We have also discovered in our research that plain silica gel selectively binds certain cations present as solutes in solution. Prior researchers who have studied the analytical applications of silica gel and macrocycle-bonded silicas have confined their investigations to chromatographic applications where ions are present in concentrations greater than the ppb range. The concentration and subsequent analysis of selected ions requires quantitative and selective complexation of the ions so that the ions may be sufficiently concentrated. The extent of macrocycle-ion or silica gel-cation interaction is particularly important when ions present in solution at low concentrations need to be complexed. The greater the value of the equilibrium constant for ion-macrocycle or cationsilica gel interaction, the lower the initial concentration of the ion in solution can be and still be efficiently and quantitatively complexed, and therefore removed from the solution. Silica gel forms strong bonds with only a few selected cations. However, various macrocycles form strong and selective bonds with numerous ions, when the macrocycles are present as solutes in solution. An extensive compilation of the association constants between macrocycles and various cations is found in an article by R. M. Izatt, J. S. Bradshaw, S. A. Nielsen, J. D. Lamb, J. J. Christensen, and D. Sen, *THERMODYNAMIC AND KINETIC DATA FOR CATION-MACROCYCLE INTERACTION,* Chem. Rev., 1985, Vol. 23, 271–339. The ability to attach these macrocycles to silica without reducing the ability of the macrocycle to complex ions is of the utmost importance in their use as a concentrator for analytical purposes. In this patent we report the successful use of bonded macrocycles and in certain instances plain silica gel for this purpose.

SUMMARY OF INVENTION

The process of recovering and concentrating the desired ion(s) is characterized by quantitatively complexing with any complexing compound, from a known volume of solution, the desired ion(s) when they are present at low concentrations and recovering the said ion(s) from the complex by bringing the complex into contact with a much smaller known volume of a receiving phase which contains a solubilizing reagent, which need not be selective, but which will strip the ion(s) from the complex quantitatively and then analyzing the concentrated ions by well known analytical procedures.

BRIEF DESCRIPTION OF THE DRAWINGS

The invention will be described and illustrated by reference to the drawings in which:

FIG. 1 represents four families of macrocycle-bonded silicas comprising some of the types of compounds to be used in this invention. These include (A) the polyether or polyazaether macrocycles (so-called crown or aza-crown compounds); (B) the polyazaether macrobicycles (so-called cryptands); (C) polypyridinoether macrocycles (so-called pyridino-crown compounds); and (D) polytriazoloether macrocycles (so-called triazolo-crown compounds).

DESCRIPTION OF THE PREFERRED EMBODIMENT OF THE INVENTION

Figure 2:
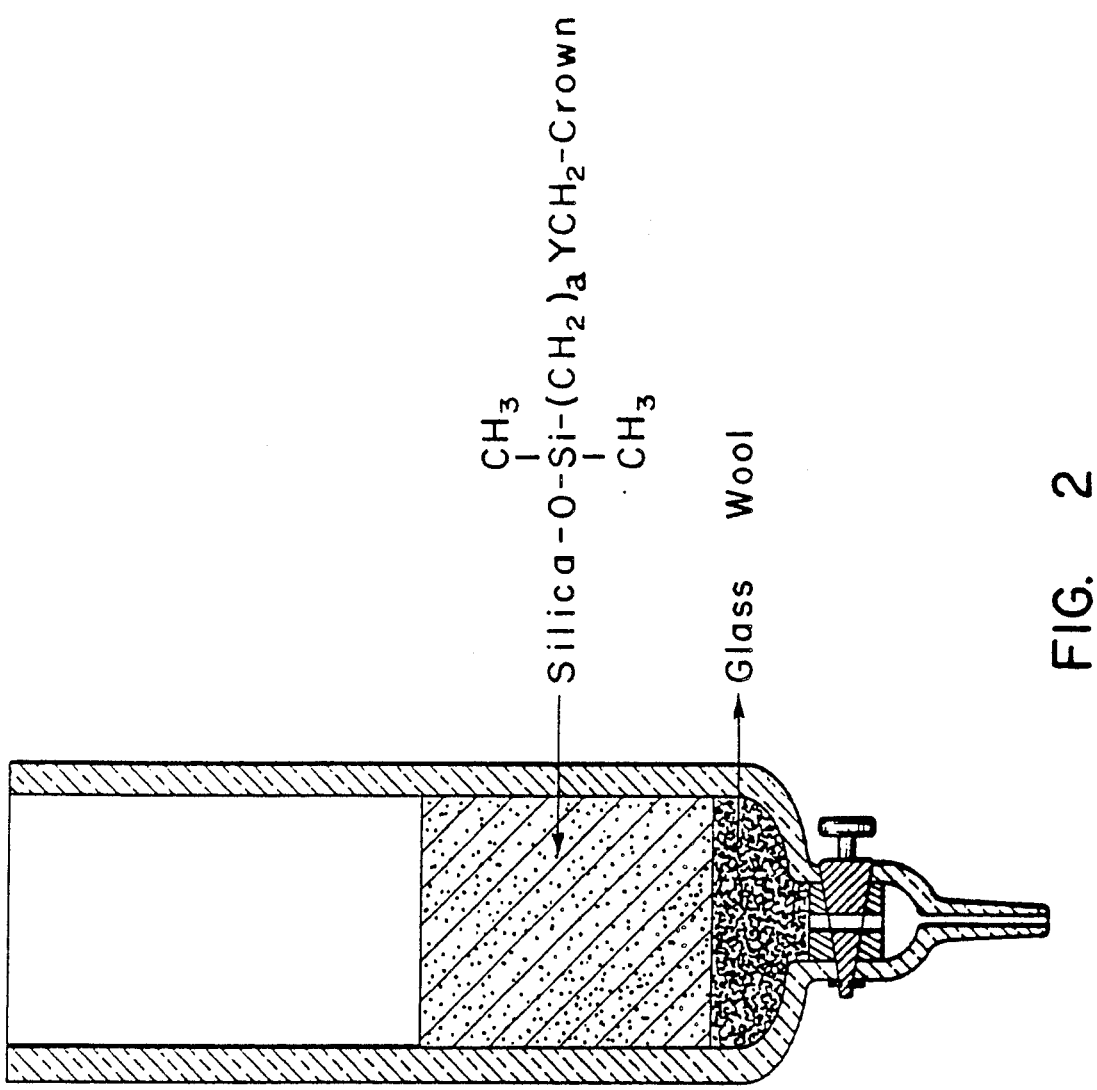
FIG. 2 represents schematically a suitable column for holding the macrocycle-bonded silica material through which a solution of metal ions can be flowed to complex selectively with a desired ion or group of ions and through which a small volume of a receiving phase can be flowed to break the complex, dissolve the desired ions and carry them out of the column.

Materials which selectively complex with the desired metal ions preferably are covalently bonded to silica. The silica material can be sand, silica particles or silica gel. One series of cation binding materials covalently bonded to silica is shown in FIG. 1. These compounds have been already disclosed and claimed by us in U.S. patent application, Ser. No. 07/093,544 by J. S. Bradshaw, R. M. Izatt, J. J. Christensen, and R. L. Bruening, MACROCYCLIC LIGANDS BONDED TO SILICA AND THEIR USE IN SELECTIVELY AND QUANTITATIVELY REMOVING AND CONCENTRATING IONS PRESENT AT LOW CONCENTRATIONS FROM MIXTURES THEREOF WITH OTHER IONS. filed Sept. 4, 1987. These compounds are examples of the many different types of cation complexing agents that can be used to concentrate the desired ions. Any material which complexes with the desired ions with a sufficient association constant can be used to concentrate the desired ions, preferably one which can be covalently bonded to silica.

The present patent does not claim the synthesis of these various silica-bound ion complexing agents, some of which are claimed in the aforementioned patent application. The present application claims the process of using these materials for the concentration and subsequent analysis of various ions in the ppb range. This will now be described in more detail in the following description of the processes of ion concentration, recovery, and analysis.

ION CONCENTRATION, RECOVERY, AND ANALYSIS PROCESSES

The ion recovery and concentration processes of the invention relate to the selective recovery of desired ions from mixtures thereof with other ions, preferably using macrocycle-bonded silica or, in a few cases, plain silica gel. The ion(s) involved may be any cation or anion which can be quantitatively complexed with a complexing agent. The synthesis of macrocycle-bonded silica is not part of the present invention as described in the previous section of this application. Effective analysis of ions present in water at concentrations below the 100 ppb level is difficult using present analytical methods. The need for quick and accurate analysis of toxic ions at these low concentrations is particularly important in the monitoring of these ions in culinary and waste water. Toxic ions such as $NO_3^-$, $CN^-$, $Pb^{2+}$, $Hg^{2+}$, $Cd^{2+}$, $Ag^+$, $Ba^{2+}$, and others need to be monitored at the ppb level. Other less toxic ions such as $Na^+$, $K^+$, $Ca^{2+}$, $Mg^{2+}$, $SO_4^{2-}$, and $Cl^-$ are also present in these solutions. Some of these latter ions, such as $Na^+$, $Ca^{2+}$, $Mg^{2+}$, etc., are present in the tens of ppm range. Hence, the need to selectively recover and concentrate the above mentioned toxic ions for analysis. Other situations where analyses in the ppb range must be made also exist. The present invention accomplishes the necessary separation and concentration effectively and rapidly, particularly by the use of macrocycle-bonded silica or in a few cases plain silica gel so that these analyses can take place.

The process first involves selecting a complexing agent e.g., a macrocycle-bonded silica or plain silica gel which will selectively and quantitatively complex the ion(s) of interest and thereby remove it from a solution which is brought into contact with the complexing agent, e.g., the macrocycle-bonded silica. There is a large data base for measurements of macrocycle-ion interactions where the macrocycle is unsubstituted and present as a solute in a solvent. Such a data base was compiled by R. M. Izatt, J. S. Bradshaw, S. A. Nielsen, J. D. Lamb, J. J. Christensen, and D. Sen, *THERMODYNAMIC AND KINETIC DATA FOR CATION-MACROCYCLE INTERACTION.* Chem. Rev., 1985, Vol. 23, 271-339. Previously, this data base has only provided general predictions of the behavior of macrocycles incorporated into separation processes in solution. However, we reported recently in U.S. patent application, Ser. No. 07/093,544, by J. S. Bradshaw, R. M. Izatt, J. J. Christensen, and R. L. Bruening, *MACROCYCLIC LIGANDS BONDED TO SILICA AND THEIR USE IN SELECTIVELY AND QUANTITATIVELY REMOVING AND CONCENTRATING IONS PRESENT AT LOW CONCENTRATIONS FROM MIXTURES THEREOF WITH OTHER IONS,* filed Sept., 4, 1987, that the equilibrium constants for ion-macrocycle interaction for macrocycles present as solutes in solution vs. that for macrocycles bonded to silica show little or no variation. It is emphasized that similar interaction of the bonded macrocycle and macrocycle in solution is only obtained when electron withdrawing groups are not attached to the macrocycle and when the macrocycle is not attached to silica via one of the donor atoms of the macrocycle. We have also made extensive measurements of the interaction of plain silica gel with cations and have found that a few particular cations do interact quantitatively and selectively with silica gel when these cations are present in the ppb range.

Once the desired ion(s) are attached to the complexing agent, e.g., the macrocycle-bonded silica, they must be removed using a volume of a receiving phase much smaller than the original volume of solution containing the desired ion(s). Furthermore, the volumes of both the original source phase and the receiving phase solutions must be known in order for the concentration factor to be calculated under these circumstances. The concentrations of the ion(s) of interest present in concentrated form in the receiving phase can be easily determined by well known analytical methods such as atomic absorption spectroscopy. The concentrations of the ion(s) of interest in the original source phase solution can then be calculated by dividing the measured receiving phase concentration by the concentration factor calculated from the relative volumes.

Examples of the successful use of the present invention to obtain accurate analyses of ion concentrations in the ppb level for solutions prepared at known concentrations will now be given. In Table 1, the analysis of $Sr^{2+}$ concentrations in $H_2O$ in the ppb range using 18-crown-6 bonded to silica gel is presented. The analysis was tested by running volumes of known $Sr^{2+}$ concentrations through a column, concentrating the $Sr^{2+}$, and analyzing the resulting solution for $Sr^{2+}$. These volumes also contained $Ca^{2+}$, $Mg^{2+}$, and $Na^+$ at concentrations present in a typical culinary water supply (see footnote b to Table 1). The 18-crown-6 macrocycle was chosen because of its selective interaction with $Sr^{2+}$ over $Ca^{2+}$ and $Na^+$ which are also present in the solution. The log of the equilibrium constant for 18-crown-6-$Sr^{2+}$ interaction is 2.72. This value is not sufficiently large for quantitative removal of $Sr^{2+}$ from a large volume of solution using the small column described above, but quantitative $Sr^{2+}$ removal by this macrocycle from a one liter volume takes place. Hence, macrocycles which selectively interact with particular ion(s) over other ions can be used in the concentration procedure even though their interaction constants may not be large. The receiving phase used to remove the $Sr^{2+}$ in a small volume was ethylenediaminetetracetic acid (EDTA). The $Sr^{2+}$ interacts more strongly with EDTA(log K=8.73) than it does with the macrocycle.

TABLE 1

Analysis of $Sr^{2+}$ Concentrations in the ppb Range Using an 18-Crown-6 Bonded Silica Gel Column[a] when $Ca^{2+}$, $Mg^{2+}$, and $Na^+$,[b] are also Present in Solution

| Known Concentration[c] (ppb) | Measured Concentration[d] (ppb) |
|---|---|
| 100 | 101 ± 5 |
| 10 | 9.3 ± 0.5 |
| 1 | 0.90 ± 0.12 |

[a]The cylindrical column used was 1.90 cm in diameter and contained a 1.5 cm height of the material. The gel capacity was 5.3 moles of macrocycle/m³ silica gel.
[b]The cations were present as the $NO_3^-$ salts and the concentrations of $Ca^{2+}$, $Mg^{2+}$, and $Na^+$ were 52 ppm, 15 ppm, and 148 ppm, respectively.
[c]The solutions were prepared at known $Sr^{2+}$ concentrations by diluting atomic absorption spectroscopy standards of known concentrations to the indicated concentrations using volumetric pipets. Any $Sr^{2+}$ present in the $Ca^{2+}$, $Mg^{2+}$ and $Na^+$ salts was removed by passing these salts in solution through an 18-crown-6 bonded silica column before the indicated amount of $Sr^{2+}$ was added.
[d]The volume of the original sample required for analysis is 100 ml, 100 ml and 1000 ml for the 100, 10, and 1 ppb levels, respectively. A solution containing 0.03 M EDTA and 0.10 M LiOH or NaOH was used as the receiving phase.

Furthermore, the EDTA was present at a greater concentration than the macrocycle. The combination of these two effects allows for the $Sr^{2+}$ to be stripped from the macrocycle in a relatively small volume. Other materials such as citric acid and acetic acid can also be used for the removal of $Sr^{2+}$ from the column. The $Sr^{2+}$ in the receiving phase was then analyzed using atomic absorption spectrophotometry, although other analytical methods could have been used. Experiments identical to those in Table 1, but using a plain silica gel column for $Sr^{2+}$ concentration and analysis were also tried. The silica gel did not quantitatively remove the $Sr^{2+}$ from the aqueous solutions under these conditions.

The data base for ion-macrocycle interactions, mentioned above, allows for the judicious choice of an appropriate macrocycle for a specific analytical need. For example, $Pb^{2+}$, $Cd^{2+}$, $Ag^+$, and $Hg^{2+}$ need to be analyzed at the ppb level in culinary water. The macrocycle diaza-18-crown-6 interacts strongly with these cations. Furthermore, this macrocycle interacts very weakly with $Ca^{2+}$, $Mg^{2+}$, $Na^+$, and $K^+$, which are the cationic species present in water in large quantities. This macrocycle could then be used to selectively and quantitatively complex $Pb^{2+}$, $Cd^{2+}$, $Ag^+$ and $Hg^{2+}$ from a culinary water sample. The diazacrown-bonded silica is shown in FIG. 1.A.3. The chemical EDTA interacts more strongly with $Pb^{2+}$, $Cd^{2+}$, $Ag^+$, and $Hg^{2+}$ than does the macrocycle. Hence, a concentrated EDTA solution could be used as the receiving phase. Finally, an inductively coupled plasma atomic absorption spectophotometer could be used to analyze the concentrated receiving phase for these cations all at the same time. Other macrocycles interact selectively with various other ions. Many of these macrocycles are proton-ionizable which allows for the use of an acid solution as the receiving phase.

Plain silica gel interacts with sufficient strength to quantitatively bind several cations when other cations are not present in excess concentrations. The determination of $Pb^{2+}$ and $Sr^{2+}$ concentrations in the ppb range has been accomplished with standard deviations similar to those of Table 1 when any other cation(s) are present in the sample at or below the ppb level. However, plain silica gel interacts selectively with only few cations. Hence, analysis at the ppb level for a particular cation when other cations are present at much higher concentrations is possible in only a few cases. An example of this is given in Table 2 for the analysis of $Pb^{2+}$ in the ppb range when $Ca^{2+}$, and $Na^+$ are present in large excess. The $Pb^{2+}$ experiments were performed by the same method described above for $Sr^{2+}$ except that plain silica gel was used as the column material. Additional $Pb^{2+}$ experiments were performed using 18-crown-6 bonded silica as the column material. The analysis data for $Pb^{2+}$ using the macrocycle-containing material is comparable to those presented in Table 2. This is to be expected since both silica gel and 18-crown-6 interact selectively with $Pb^{2+}$ over $Ca^{2+}$, and $Na^+$.

The detection limits of the processes described above is dependent on the concentration factor (volume of the source solution divided by the volume of the receiving solution) and the detection limit of the analytical method used. For example, the detection limits for $Sr^{2+}$ and $Pb^{2+}$ are 0.2±0.2 ppb and 0.5±0.5 ppb, respectively, if the concentration factor is 100 and inductively coupled plasma atomic absorption spectroscopy is the analytical method used.

In conclusion, many ions can be analyzed in the ppb range by concentrating the ions of interest using a complexing agent, e.g., a macrocycle-bonded silica or in a few cases plain silica gel followed by the recovery of the ions in a smaller volume of a receiving phase. This process is effective even when other ions are present in the original solution in large excess since macrocycles are highly selective in their interaction with ions. The large data base for macrocycle-ion interaction allows for a judicious choice of the appropriate macrocycle for a desired analysis under a particular set of circumstances.

TABLE 2

Analysis of $Pb^{2+}$ Concentrations in the ppb Range Using a Plain Silica Gel Column[a] when $Ca^{2+}$, $Mg^{2+}$, and $Na^+$,[b] are also Present in Solution

| Known Concentration[c] (ppb) | Measured Concentration[d] (ppb) |
|---|---|
| 100 | 97 ± 11 |
| 10 | 9.0 ± 0.7 |

[a]The cylindrical column used was 1.90 cm in diameter and contained a 2.5 cm height of the material.
[b]The cations were present as the $NO_3^-$ salt and the concentrations of $Ca^{2+}$, $Mg^{2+}$, and $Na^+$ were 52 ppm, 15 ppm, and 148 ppm, respectively.
[c]The solutions were prepared at known $Pb^{2+}$ concentrations by diluting atomic absorption spectroscopy standards of known concentrations to the indicated concentrations using volumetric pipets. Any $Pb^{2+}$ present in the $Ca^{2+}$, $Mg^{2+}$, and $Na^+$ salts was removed by passing these salts in solution through an 18-crown-6 bonded silica column before the indicated amount of $Pb^{2+}$ was added.
[d]The volume of the original sample required for analysis is 100 ml and 1000 ml for the 100 and 10 ppb levels, respectively. A solution containing 0.03 M EDTA and 0.10 M LiOH or NaOH was used as the receiving phase.

Although the invention has been described and illustrated in connection with specific examples of processes using specific compounds, it will be understood that modifications and variations are contemplated and may be made without departing from the spirit and scope of the invention as defined in the following claims.

We claim:

1. The method of selectively and quantitatively removing and concentrating at least one selected ion from a multiple ion solution in which other ions are present, said method comprising:

(a) bringing a complexing agent for the selected ion(s) into contact with said multiple ion solution to remove and concentrate selected ion(s) from the multiple ion solution, wherein said complexing agent is selected from the group of macrocyclic compounds having at least four —A—CH$_2$—CH$_2$— groups in which A is selected from O, O—CH$_2$, S, S—CH$_2$, N—R and N—R—CH$_2$ in which R is selected from H, lower alkyl and benzyl and which has a hydrocarbon side chain having an end group

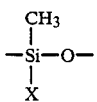

covalently bonded to silica in which X is selected from lower alkyl, benzyl, phenyl, halogen, O—CH$_3$, O—C$_2$H$_5$ and Si;

(b) removing the multiple ion solution from which the complexing agent has removed the selected ion(s) from the complexing agent having the selected ion(s) complexed therewith;

(c) bringing the complexing agent complexed with selected ion(s) into contact with a receiving liquid to break the complex and remove the selected and concentrated ion(s) from the complexing agent; and (d) determining the concentration of selected ion(s) in said receiving liquid from which the concentration of selected ion(s) in the multiple ion solution can be calculated.

2. The method as set forth in claim 1 in which the selected ion is a heavy metal ion.

3. The method as set forth in claim 2 in which the heavy metal ion is selected from the group consisting of lead, silver, cadmium and mercury.

4. The method as set forth in claim 1 in which the complexing agent is a macrocyclic compound selected from the group consisting of

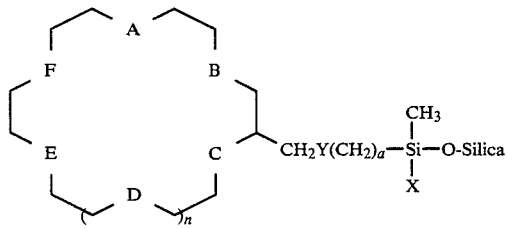

A–F = any combination of O or OCH$_2$ or S or SCH$_2$ or N—R or N(R)CH$_2$ (R = H or any alkyl or benzyl); n = −1 to 4; X = any alkyl or Cl or O-Silica; Y = O or CH$_2$; a = 1-16.

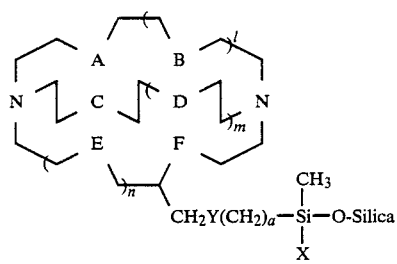

A–F = any combination of O or S or N—R (R = H or any alkyl or benzyl); l, m, n = 0-2; X = any alkyl or Cl or O-Silica; Y = O or CH$_2$; a = 1-16.

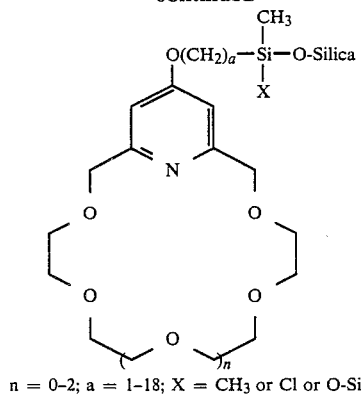

n = 0-2; a = 1-18; X = CH$_3$ or Cl or O-Silica;

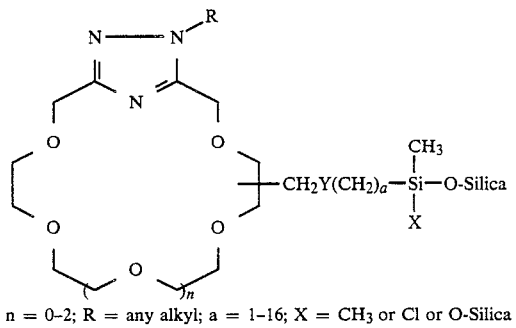

n = 0-2; R = any alkyl; a = 1-16; X = CH$_3$ or Cl or O-Silica in which Silica is sand or silica gel.

5. A process of separating a selected ion from a plurality of other ions in a multiple ion solution as set forth in claim 1 comprising flowing the multiple ion solution through a column packed with a composition of matter having the structural formula:

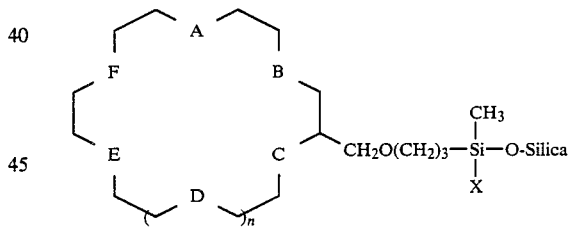

A–F=O; n=0-2; X=CH$_3$ or Cl or O-Silica.

6. A process of separating a selected ion from a plurality of other ions in a multiple ion solution as set forth in claim 1 comprising flowing the multiple ion solution through a column packed with a composition of matter having the structural formula:

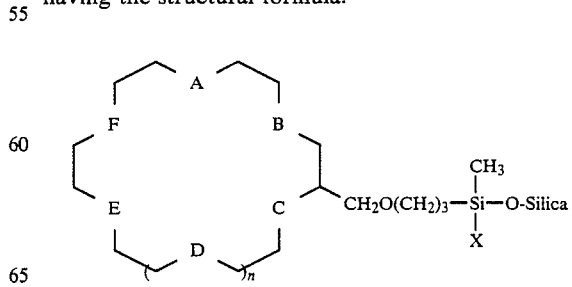

A,C,D,F=O; B and E=N—R (R=H or alkyl or benzyl);

n=0-2; X=CH₃ or Cl or O-Silica.

7. A process of separating a selected ion from a plurality of other ions in a multiple ion solution as set forth in claim 1 comprising flowing the multiple ion solution through a column packed with a composition of matter having the structural formula:

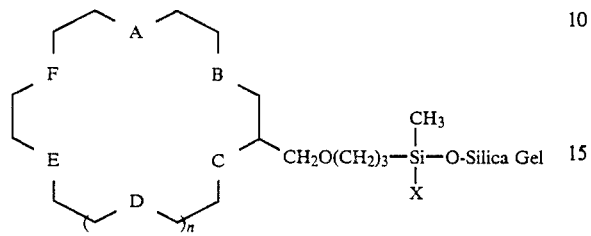

A–F=any combination of O or S or N—R (R=H or any alkyl or benzyl); n=0–4;

X=any alkyl or Cl or O-Silica Gel.

8. A process of separating a selected ion from a plurality of other ions in a multiple ion solution as set forth in claim 1 comprising flowing multiple ion solution through a column packed with a composition of matter having the structural formula:

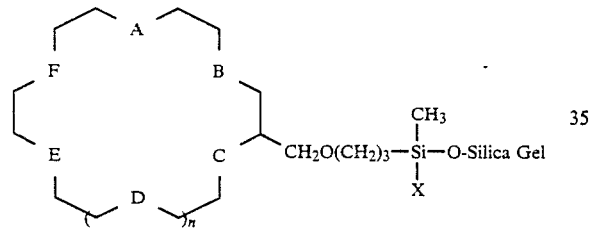

A–F=O; n=0–2; X=CH₃ or Cl or O-Silica Gel.

9. A process of separating selected ion from a plurality of other ions in a multiple ion solution as set forth in claim 1 comprising flowing multiple ion solution through a column packed with a composition of matter having the structural formula:

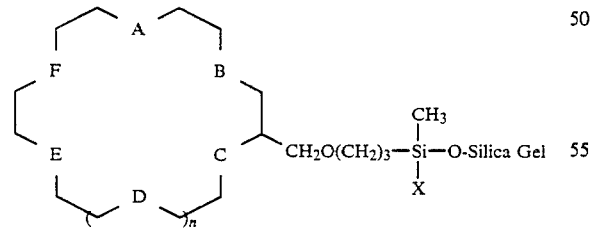

A,C,D,F=O; B and E=N—R (R=H or alkyl or benzyl);

n=0–2; X=CH₃ or Cl or O-Silica Gel.

10. A process of separating a selected ion from a plurality of other ions in a multiple ion solution as set forth in claim 1 comprising flowing the multiple ion solution through a column packed with a composition of matter having the structural formula:

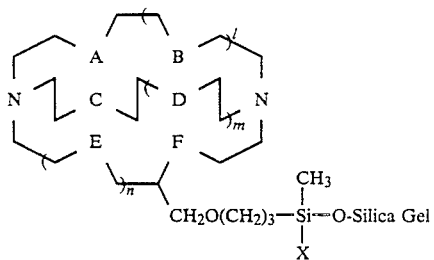

A–F=any combination of O or S or N—R (R=H or any alkyl or benzyl); l, m, n=0–2;

X=any alkyl or Cl or O-Silica Gel.

11. A process of separating a selected ion from a plurality of other ions in a multiple ion solution as set forth in claim 1 comprising flowing the multiple ion solution through a column packed with a composition of matter having the structural formula:

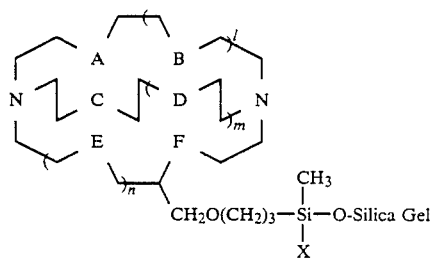

A–F=O; l=m=n=1; X=CH₃ or Cl or O-Silica Gel.

12. A process of separating a selected ion from a plurality of other ions in a multiple ion solution as set forth in claim 1 comprising flowing the multiple ion solution through a column packed with a composition of matter having the structural formula:

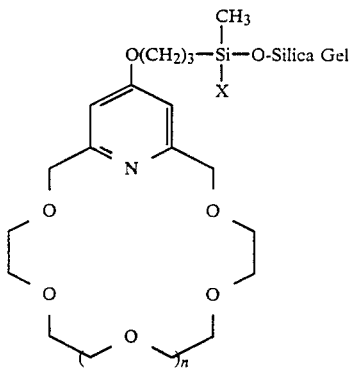

n=0–2; X=CH₃ or Cl or O-Silica Gel.

13. A process of separating a selected ion from a plurality of other ions in a multiple ion solution as set forth in claim 1 comprising flowing the multiple ion solution through a column packed with a composition of matter having the structural formula:

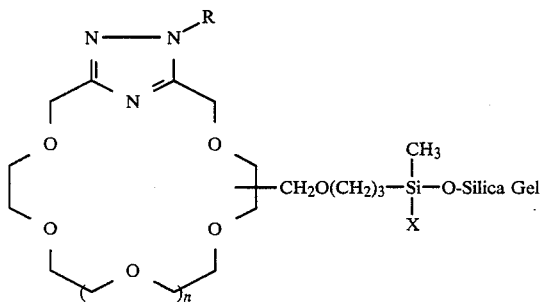

n=0-2; R=any alkyl;
X=CH₃ or Cl or O-Silica Gel.

14. The process of determining the heavy metal ion(s) content of drinking water which comprises flowing the drinking water in measured quantity through a column packed with silica covalently bonded to a complexing agent for the heavy metal ion(s), wherein said complexing agent is selected from the group of macrocyclic compounds having at least four —A—CH₂—CH₂— groups in which A is selected from O, O—CH₂, S, S—CH₂, N—R and N—R—CH₂ in which R is selected from H, lower alkyl and benzyl and which has a hydrocarbon side chain having an end group

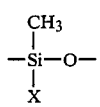

covalently bonded to silica in which X is selected from lower alkyl, benzyl, phenyl, halogen, O—CH₃, O—C₂H₅ and Si; flowing a receiving liquid through said column to break the complex and take the liberated ions into solution; analyzing the solution to determine the amount of heavy metal ion(s) therein; and calculating therefrom the concentration of heavy metal ion(s) in the drinking water.

15. A method of achieving the selective and quantitative removal of a selected ion or group of ions from a plurality of ions in a multiple ion solution by bringing a known amount of the solution into contact with a macrocyclic compound selected from the group consisting of:

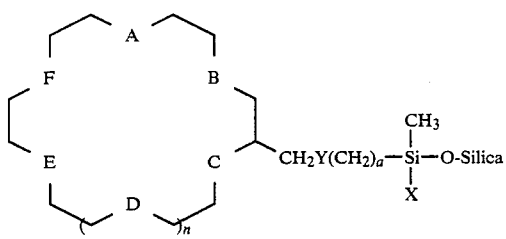

A–F = any combination of O or S or N—R (R = H or any alkyl or benzyl); n = 0–4; X = any alkyl or Cl or O-Silica; Y = O or CH₂; a = 1–16.

-continued

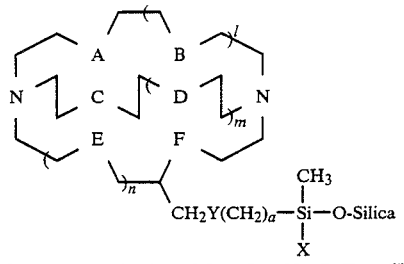

A–F = any combination of O or S or N—R (R = H or any alkyl or benzyl); l, m, n = 0–2; X = any alkyl or Cl or O-Silica; Y = O or CH₂; a = 1–16.

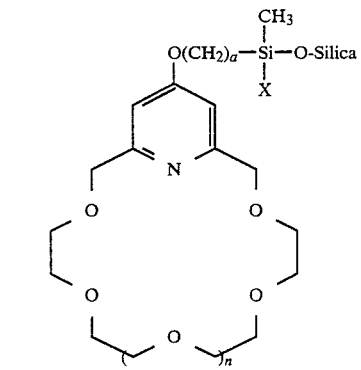

n = 0–2; a = 1–18; X = CH₃ or Cl or O-Silica;

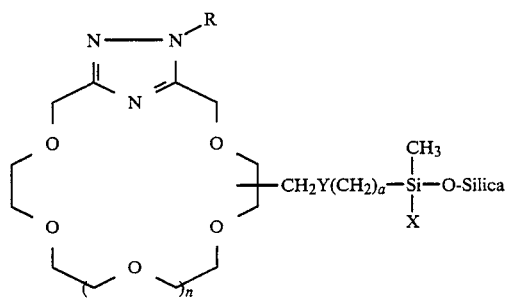

n = 0–2; R = any alkyl; a = 1–16; X = CH₃ or Cl or O-Silica

In which Silica is sand or silica gel,
concentrating at least one selected ion which has been complexed with said macrocyclic compound by eluting it with a receiving liquid and determining the concentration thereof in said receiving liquid.

16. The process as set forth in claim 15 in which said silica is silica gel.

17. The process as set forth in claim 15 in which said silica is sand.

18. The process as set forth in claim 15 in which the ions to be separated, concentrated and analyzed are metal cations.

19. The process as set forth in claim 15 in which the receiving liquid contains a complexing agent selected from the group consisting of ethylenediaminetetraacetic ions, citrate ions and acetate ions.

20. The process as set forth in claim 15 in which the ions are analyzed by atomic adsorption spectroscopy and/or ion chromatography.

* * * * *